United States Patent
Coupan et al.

(10) Patent No.: US 11,891,706 B2
(45) Date of Patent: Feb. 6, 2024

(54) GAS TO HYDROGEN PROCESS WITH CO-PRODUCTION OF CARBON

(71) Applicants: TOTALENERGIES ONETECH, Courbevoie (FR); SULZER MANAGEMENT AG, Winterhur (CH)

(72) Inventors: Romuald Coupan, Vanves (FR); Nikolai Nesterenko, Nivelles (BE); Gleb Veryasov, Nivelles (BE)

(73) Assignees: TOTALENERGIES ONETECH, Courbevoie (FR); SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 17/915,958

(22) PCT Filed: Mar. 29, 2021

(86) PCT No.: PCT/EP2021/058138
§ 371 (c)(1),
(2) Date: Sep. 29, 2022

(87) PCT Pub. No.: WO2021/198168
PCT Pub. Date: Oct. 7, 2021

(65) Prior Publication Data
US 2023/0118848 A1    Apr. 20, 2023

(30) Foreign Application Priority Data

Mar. 30, 2020 (EP) ..................................... 20315076

(51) Int. Cl.
C25B 1/02      (2006.01)
C01B 32/05     (2017.01)
(Continued)

(52) U.S. Cl.
CPC ................ C25B 1/02 (2013.01); C01B 7/093 (2013.01); C01B 32/05 (2017.08); C01B 32/205 (2017.08);
(Continued)

(58) Field of Classification Search
CPC ......... C01B 32/05; C01B 32/205; C25B 1/24; C25B 1/02
See application file for complete search history.

(56) References Cited

U.S. PATENT DOCUMENTS

2009/0308759 A1   12/2009  Waycuilis

FOREIGN PATENT DOCUMENTS

| GB | 2571248 A | 8/2019 | |
| WO | 2008/143940 A1 | 11/2008 | |
| WO | WO-2010009376 A1 * | 1/2010 | .............. B01J 29/44 |

OTHER PUBLICATIONS

Search Report dated Jun. 7, 2021 issued in corresponding International Application No. PCT/EP2021/058138.
(Continued)

*Primary Examiner* — Nicholas A Smith
(74) *Attorney, Agent, or Firm* — Nath, Goldberg & Meyer; Joshua B. Goldberg (57) ABSTRACT

The disclosure relates in its first aspect to a process of conversion of a gaseous stream comprising methane into hydrogen (51) and carbon (25), the process is remarkable in that it comprises a step (a) of providing a first gaseous stream (3, 7); a step (b) of bromination and synthesis in which the first gaseous stream (3, 7) is put in contact with a second stream (53) comprising bromine resulting in the formation of a third stream (15) comprising methyl bromides and hydrogen bromide, and of a fourth stream (25) comprising carbon including graphite and/or carbon black; a step (c) of separation performed on the third stream (15) to
(Continued)

recover a hydrogen bromide-rich stream (41) which is then oxidized in a step (d) to produce a stream (51) comprising hydrogen. The second aspect relates to the installation for performing the process of the first aspect and the third aspect concerns the use of bromine in such process.

14 Claims, 5 Drawing Sheets

(51) Int. Cl.
    *C25B 15/08*     (2006.01)
    *C01B 7/09*     (2006.01)
    *C25B 1/04*     (2021.01)
    *C25B 1/24*     (2021.01)
    *C01B 32/205*     (2017.01)
    *C25B 5/00*     (2006.01)

(52) U.S. Cl.
    CPC .................. *C25B 1/04* (2013.01); *C25B 1/24* (2013.01); *C25B 15/085* (2021.01); *C25B 5/00* (2013.01)

(56) References Cited

OTHER PUBLICATIONS

Written Opinion dated Jun. 7, 2021 issued in corresponding International Application No. PCT/EP2021/058138.
Direct/Informal comments regarding search in priority application No. EP 20315076.8 dated Mar. 29, 2021.

* cited by examiner

GAS TO HYDROGEN PROCESS WITH CO-PRODUCTION OF CARBON

This is a National Phase Application filed under 35 U.S.C. 371 as a national stage of PCT/EP2021/058138, filed Mar. 29, 2021, an application claiming the benefit of European Application No. 20315076.8, filed Mar. 30, 2020, the content of each of which is hereby incorporated by reference in its entirety.

FIELD OF THE DISCLOSURE

The present disclosure relates to gas to hydrogen processes.

TECHNICAL BACKGROUND

Natural gas is an available fossil resource mainly composed of light alkanes. The valorisation of natural gas as feedstock for the petrochemical industry is of interest as natural gas is cheap at source. Accordingly, the conversion of light alkanes into products like syngas, methanol, olefins or aromatics is highly valuable.

Oxygen-based processes are the current practices for natural gas conversion. However, processes involving the presence of oxygen leads unavoidably to the formation of carbon dioxide and water in the final product streams. The carbon efficiency of any processes contacting alkanes and oxygen does not exceed 75%.

Recently, technology like the Gas-to-Aromatics (G2A) technology from GTC Technologies based on bromine-mediated activation of methane, was developed. The G2A process aims at converting methane to liquid hydrocarbons i.e. C6-C9 aromatics, C5 and C10+ products. In such a process, hydrogen bromide, which is a by-product of activation of methane, is recycled back to bromine consuming oxygen and coproducing water. This first-generation technology thus offers a low carbon way to transform methane to chemicals and water with high carbon efficiency of about 85%. Current G2A technology is nevertheless not an oxygen-free process as oxygen is used for bromine recovery and produces water.

The reforming process is the most practical current commercial process i.e. Steam Methane Reforming (SMR), Auto-Thermal Reforming (ATR), Dry Methane Reforming (DMR), Partial Oxidation Reforming (PDX).

The process of reforming of methane (SMR, ATR, DMR, PDX) is exemplified by the following chemical equations.

$$CH_4 + H_2O \rightarrow CO + 3H_2 \quad \text{SMR:}$$

$$2CH_4 + O_2 \rightarrow 2CO + 4H_2 \quad \text{ATR/PDX:}$$

$$CH_4 + CO_2 \rightarrow 2CO + 2H_2 \quad \text{DMR:}$$

The methane reforming process produces synthesis gas (i.e. a mixture of carbon monoxide and hydrogen) that can be further converts to liquid hydrocarbons in the Gas-to-Liquid process (GTL) or to methanol in the Gas-to-Methanol process (GTM), as indicated in the following two chemical equations:

$$nCO + (2n+1)H_2 \rightarrow C_nH_{2n+2} + nH_2O \quad \text{GTL:}$$

$$CO + 2H_2 \rightarrow CH_3OH \quad \text{GTM:}$$

Also, methanol can be used as feedstock in processes such as Methanol-to-Gasoline (MTG), Methanol-to-Olefins (MTO), and Methanol-to-Propylene (MTP).

The conversion of methanol (MTG, MTO, MTP) can be summarized by the following chemical equation.

$$nCH_3OH \rightarrow C_nH_{2n} + nH_2O$$

In recent times, the Oxidative Coupling of Methane (OCM) was developed. It consists of a direct catalytic oxygen-based process to convert methane into ethylene as shown in the following chemical equation:

$$2CH_4 + O_2 \rightarrow C_2H_4 + 2H_2O$$

All oxidative conversion processes imply the formation of carbon dioxide and water in the final product streams.

$$CH_4 + 2O_2 \rightarrow CO_2 + 2H_2O$$

The issue with the formation of carbon dioxide and water is then their further transformation into valuable chemicals, such as the conversion of water into hydrogen and the reaction of the hydrogen with the carbon dioxide to form various useful chemical is highly demanding in energy. There is thus a need for reactivation of these compounds at low energy costs.

It is known that natural gas, and methane, in particular, can be activated via bromination. In this case, the cost of activation of methane can be significantly lowered since processes for bromine recovery are available, such as electrolysis, as described in US 2009/0308759. Such a process has also the advantage of producing hydrogen.

GB 2571248 describes a method for the production of a graphene layer structure. The precursor compound can be an organic compound such as dibromomethane.

It would be valuable to design a process that allows the production of additional chemicals, such as carbon (graphite, carbon black . . . ). For instance, carbon black is notably used as reinforcing filler in rubber product or as a color pigment. However, the production of carbon black is often produced by the incomplete combustion of heavy petroleum product, which is not environmentally friendly.

It is thus desirable to have a technology that is environmentally friendly and which can generate useful products to maximize the potential of natural gas and methane in particular.

SUMMARY OF THE DISCLOSURE

According to a first aspect, the disclosure provides a process of conversion of a gaseous stream comprising methane into hydrogen and carbon, said process being remarkable in that it comprises the following steps:
- a step (a) of providing a first gaseous stream comprising methane ($CH_4$);
- a step (b) of bromination and synthesis of carbon wherein the first gaseous stream comprising methane ($CH_4$) of step (a) is put in contact with a second stream comprising bromine ($Br_2$) under operating conditions resulting in the formation of a third stream comprising methyl bromides ($CH_{4-n}Br_n$) and hydrogen bromide, and of a fourth stream comprising carbon including graphite and/or carbon black;
- a step (c) of separation performed on the third stream to recover a hydrogen bromide (HBr) stream and a methyl bromides-rich stream, wherein the process comprises a step of recycling the methyl bromides-rich stream into step (b) of bromination and synthesis of carbon; and
- a step (d) of converting said hydrogen bromide-rich stream into a stream comprising hydrogen and a stream comprising bromine.

Surprisingly, it has been found that it is possible to produce hydrogen from methane without forming water and/or carbon dioxide but forming carbon instead. The process according to the disclosure allows converting methane to hydrogen based on bromine-mediated activation of methane. Since the bromine can be recovered by oxidation of hydrogen bromide, the process according to the present disclosure allows producing hydrogen using renewable energy. The process further allows enhancing the formation of carbon by recovering and recycling methyl bromides, namely $CH_{4-n}Br_n$.

For example, n is a natural number equal to 1, 2 or 3. With preference, n equal to 1.

With preference, the process of conversion of a gaseous stream comprising methane into hydrogen and carbon is a process of conversion of a gaseous stream comprising methane into hydrogen and carbon black and/or graphite.

For example, one or more of the following can be used to better define the step (a) of providing a first gaseous stream comprising methane:
- Step (a) of providing a first gaseous stream comprising methane comprises providing a natural gas comprising methane at a content of at least 75 mol. % of the total molar content of said natural gas, preferably of at least 85 mol. %, more preferably of at least 90 mol. %, even more preferably of at least 95 mol. %.
- Step (a) of providing a first gaseous stream comprising methane comprises providing natural gas and purifying the natural gas to remove one or more selected from sulphur, nitrogen, water, oxygen and carbon dioxide.

For example, one or more of the following can be used to better define step (b) of bromination and synthesis of carbon:
- Step (b) of bromination and synthesis of carbon is performed without a catalyst.
- The operating conditions of step (b) include a temperature of at least 400° C.; preferably ranging from 400° C. to 1000° C.; more preferably from 500° C. to 1000° C. or from 500° C. to 900° C.; even more preferably from 600° C. to 800° C.
- The operating conditions of step (b) include a pressure of at least 0.1 MPa; preferably ranging from 0.1 MPa to 2.0 MPa; more preferably ranging from 0.5 to 1.5 MPa, and more preferably ranging from 0.6 to 1.0 MPa.

In a first alternative, said step (c) is performed by non-aqueous extraction and said step (d) of converting said hydrogen bromide-rich stream is performed by electrolysis of said hydrogen bromide-rich stream. With preference, said electrolysis is performed under a gaseous phase or a liquid phase.

In a second alternative, said step (c) is performed by aqueous extraction and said step (d) of converting said hydrogen bromide-rich stream is performed by electrolysis carried out in aqueous phase to produce a stream comprising bromine. With preference, said stream comprising bromine is decanted before being reused in step (b).

In a third alternative, said step (c) is performed by non-aqueous extraction and said step (d) of converting said hydrogen bromide-rich stream is carried out in presence of an oxygen stream, to produce a bromine-rich stream which is optionally reused in step (b). With preference, said bromine-rich stream is reused in step (b) and is washed and/or dried before being reused in step (b). Wherein said step (d) of converting said hydrogen bromides-rich stream into a stream comprising hydrogen and a stream comprising bromine further produces thermal energy, wherein said thermal energy is converted into electrical energy. With preference, said electrical energy is used in an electrolysis reaction of water to produce a hydrogen stream and/or an oxygen stream which is optionally used in said step (d) of converting said hydrogen bromides-rich stream into a stream comprising hydrogen and a stream comprising bromine.

For example, one or more of the following can be used to better define step (c) of separation.
- Step (c) of separation comprises at least one step of separation of methyl bromides ($CH_{4-n}Br_n$).
- Step (c) of separation comprises at least one step of separation of hydrogen bromide (HBr).
- Step (c) of separation is performed at a temperature lower than the temperature used in step (b) of bromination and synthesis of carbon.
- Step (c) of separation comprises at least one step of separation of methyl bromides to produce a methyl bromides-rich stream wherein said separation step is performed at a temperature lower than the temperature used in step (b) of bromination and synthesis of carbon.
- Step (c) of separation comprises at least one step of separation of methyl bromides to produce a methyl bromides-rich stream and/or at least one step of separation of hydrogen bromide to produce a hydrogen bromide-rich stream.
- Step (c) of separation comprises at least one step of separation of hydrogen bromide to produce a hydrogen bromide-rich stream, wherein said hydrogen bromide rich-stream is subjected to one or more further steps of separation; preferably, the one or more further steps of separation are performed in one or more extractive distillation system using at least one solvent, preferably said at least one solvent is selected from alcohol, ketone, carboxylic acid, ketone, organobromine compounds, ionic liquid, organic acid anhydride and/or nitrile.
- Step (c) of separation comprises at least one step of separation of hydrogen bromide to produce a hydrogen bromide-rich stream, wherein said hydrogen bromide rich-stream is subjected to one or more further steps of separation, and the one or more further steps of separation include steps of adjusting the temperature of the hydrogen bromide-rich stream before it reaches an extractive distillation system.
- Step (c) of separation comprises at least one step of separation of a stream comprising unreacted methane; with preference, said stream comprising unreacted methane is recycled into the first gaseous stream comprising methane.

For example, one or more of the following can be used to better define the step (d) of electrolysis:
- Step (d) of electrolysis is performed under temperature conditions ranging between 300° C. and 700° C., preferably between 350° C. and 650° C., more preferably between 400° C. and 600° C.
- Step (d) of electrolysis is performed under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.
- Step (d) of electrolysis is performed under gas-phase conditions.
- The process comprises a step of recycling the stream comprising bromine obtained in step (d) into step (b) of bromination and synthesis of carbon. With preference, the stream comprising bromine obtained in step (d) and the second stream comprising bromine of step (b) is the same.

The fourth stream including graphite and/or carbon black may consist of graphite and/or carbon black or essentially consist of graphite and/or carbon black. Should not all the carbon of the fourth stream be converted to graphite and/or carbon black, step (b) may comprise a carbonization step performed on the fourth stream.

For example, the carbonization step is performed at a temperature ranging from 500° C. to 3500° C. For example, the carbonization step is performed at a temperature ranging from 750° C. to 2000° C. For example, the carbonization step is performed at a temperature ranging from 2600° C. to 3500° C.

According to a second aspect the disclosure provides for an installation for carrying out the process of conversion of a gaseous stream comprising methane into hydrogen and carbon according to the first aspect, said installation is remarkable in that it comprises:
- a bromination and synthesis unit;
- a separation unit; and wherein the bromination and synthesis unit and the separation unit are fluidically connected in series, wherein the separation unit is arranged downstream of the bromination and synthesis unit, wherein said installation further comprises a line to convert a hydrogen bromide-rich stream into a stream comprising bromine, and wherein said installation further comprises a first line to recycle a $CH_{4-n}Br_n$-rich stream exiting the separation unit back to the bromination and synthesis unit.

For example, n is a natural number equal to 1, 2 or 3. With preference, the first line recycles a $CH_3Br$-rich stream exiting the separation unit back to the bromination and synthesis unit.

In a first alternative, said line to convert a hydrogen bromide-rich stream into a stream comprising bromine advantageously comprises an electrolysis unit. For example, said installation further comprises a bromine-recovery unit downstream of said electrolysis unit and upstream of said bromination and synthesis unit. Optionally, said electrolysis unit is comprised within said separation unit.

In a second alternative, said line to convert a hydrogen bromide-rich stream into a stream comprising bromine comprises a converting unit. With preference, said converting unit has a conversion reactor coupled with a water electrolysis unit.

For example, the bromination and synthesis unit comprises at least one reactor selected from a fixed bed reactor and/or a fluidized bed reactor.

For example, the separation unit comprises one or more distillation column and/or one or more adsorption column and/or one or more absorption column.

For example, one or more of the following can be used to better define the installation:
- The installation comprises a second line to recycle a stream comprising bromine back to the bromination and synthesis unit.
- The installation comprises a third line to recycle methane-rich stream exiting the separation unit back to the bromination and synthesis unit.
- The installation comprises a purification unit disposed upstream to the bromination and synthesis unit; preferably, the purification unit comprises at least one or more selected from a sulphur-removal system, a dryer system, a nitrogen-removal system, an oxygen-removal system or a carbon dioxide-removal system; more preferably, the purification unit comprises at least one sulphur-removal system.
- For example, the installation comprises at least one electrothermal fluidized bed reactor and a line to direct a fourth stream one or more of the reactors of the bromination and synthesis unit to the at least one electrothermal fluidized bed reactor According to a third aspect, the disclosure provides for a use of bromine in a process to produce hydrogen from methane; the use being remarkable in that the process further produces carbon and is according to the first aspect.

According to a fourth aspect, the disclosure provides for a use of an installation in a process to produce hydrogen from methane; the use being remarkable in that the installation is according to the second aspect.

DETAILED DESCRIPTION

For the disclosure, the following definitions are given:

The feed gas of the process, i.e. the first gaseous stream comprising methane, is preferably natural gas and/or other rich-methane hydrocarbon source assumed to be treated in outside battery limit (OSBL) plant where the majority of one or more selected from sulphur-containing compounds, water, carbon dioxide, oxygen and nitrogen are removed.

The expression "methyl bromides" encompasses a family of compounds having the chemical structure of the type $CH_{4-n}Br_n$, with n being an integer from 1 to 4. For instance, when n=2, the chemical structure is $CH_2Br_2$, which corresponds to the chemical structure of dibromomethane. The name "methyl bromide" is the member of the family of methyl bromides corresponding to the chemical formula $CH_3Br$, having thus n=1.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The process and the installation for carrying out the process will be jointly described by reference to FIGS. 1 to 4.

The disclosure provides a process and an installation 1 for the conversion of a gaseous stream comprising methane (3, 7) into hydrogen 51 and carbon 25. The carbon 25 which is obtained from the process can be thermally treated (by performing for example a carbonization step preferably in an electrothermal fluidized bed reactor) to produce carbon black and/or graphite, preferably carbon black. For example, the temperature which is required to produce carbon black is comprised between at least 500° C. and below 3000° C., preferably between 750° C. and 2000° C. When the temperature is above 2600° C., and up to 3500° C., the production of graphite is favoured. Preferably, graphite is formed at a temperature comprised between 3000° C. and 3400° C.

The process of conversion of a gaseous stream comprising methane (3, 7) into hydrogen (51, 63) and carbon 25, is remarkable in that it comprises the following steps:
  a step (a) of providing a first gaseous stream (3, 7) comprising methane;
  a step (b) of bromination and synthesis of carbon wherein the first gaseous stream (3, 7) comprising methane of step (a) is put in contact with a second stream (53, 95, 127) comprising bromine under operating conditions resulting in the formation of a third stream 15 comprising methyl bromides and hydrogen bromide, and of a fourth stream 25 comprising carbon including graphite and/or carbon black;
  a step (c) of separation performed on the third stream 15 to recover a hydrogen bromide-rich stream (33, 41, 107); and a methyl bromides-rich stream 23, wherein the process comprises a step of recycling the methyl bromides-rich stream 23 into step (b) of bromination and synthesis of carbon; and
  a step (d) of converting said hydrogen bromide-rich stream (33, 41, 107) into a stream (51, 63) comprising hydrogen and a stream (53, 95, 127) comprising bromine.

The first gaseous stream (3,7) is the feed stream of the process. According to the disclosure, the first gaseous stream (3,7) is or comprises natural gas. For example, the first gaseous stream (3,7) is a natural gas comprising methane. For example, a natural gas (3,7) comprising methane at a content of at least 75 mol. % of the total molar content of said natural gas; preferably at least 85 mol. %, more preferably at least 90 mol. %, and even more preferably of at least 95 mol. % of methane.

Examples of a suitable first gaseous stream (3,7) that may be used in embodiments of the process of the present invention include, but are not limited to, natural gas, coalbed methane, regasified liquefied natural gas, gas derived from gas hydrates, clathrates or both, gas derived from anaerobic decomposition of organic matter or biomass, synthetically produced natural gas or alkanes, and mixtures thereof.

The first gaseous stream (3,7) comprises methane, but in a more general way, may comprise alkanes. The alkanes present in the first gaseous stream may include, for example, lower molecular weight alkanes. As used herein, the term "lower molecular weight alkanes" refers to methane, ethane, propane, butane, pentane, or mixtures thereof. For example, the process includes a step of separation of at least a part of the alkanes other than methane performed on the first gaseous stream before said first gaseous stream enters the bromination and synthesis unit, to produce a first gaseous stream enriched in methane.

For example, the first gaseous stream 3 is submitted to an optional preliminary step of purification to remove one or more selected from sulphur, nitrogen, water, oxygen and carbon dioxide. Said purification step is performed in a purification unit 5 arranged upstream of a bromination and synthesis unit 13. The purification unit 5 may include one or more selected from sulphur removal system, a dryer system, a carbon dioxide removal system and a nitrogen removal system. These systems are well-known to the person skilled in the art and will not be further described. After purification, the first gaseous stream 7 comprises less than 2 mol % based on the total molar content of the first gaseous stream 7 of carbon dioxide; preferably less than 1 mol %, more preferably less than 0.5 mol %. After purification, the first gaseous stream 7 comprises less than 0.001 mol % based on the total molar content of the first gaseous stream 7 of sulphur components; preferably less than 0.0005 mol %.

The purified first gaseous stream 7 exiting the purification unit 5 is conveyed to the bromination and synthesis unit 13.

Before entering the bromination and synthesis unit 13 to perform step (b), the first gaseous stream 7 may pass through a heat exchanger 9 to increase its temperature.

The bromination and synthesis unit 13 comprises at least one reactor 11 selected from a fixed bed reactor and/or a fluidized bed reactor. The one or more reactors are operated under operating conditions.

The operating conditions of step (b) include a temperature of at least 400° C.; preferably ranging from 400° C. to 1000° C.; more preferably 450° C. to 950° C.; even more preferably from 500° C. to 900° C. or from 500° C. to 1000° C. For example, the operating conditions of step (b) include a temperature of at least 450° C., preferably of at least 475° C., more preferably of at least 500° C. and/or at most 1000° C., preferably at most 950° C., more preferably at most 900° C.

The operating conditions of step b) include a pressure of at least 0.1 MPa; preferably, ranging from 0.1 MPa to 2.0 MPa; more preferably ranging from 0.5 to 1.5 MPa, and more preferably ranging from 0.6 to 1.0 MPa.

The first gaseous stream (3,7), preferably being a purified first gaseous stream 7, enters the bromination and synthesis unit 13 and is put into contact with a second stream comprising bromine. Said second stream can comprise fresh bromine and/or a recycled stream comprising bromine (53, 95, 127).

Optionally, the reactor 11 can be a single reactor divided into a first zone in which the bromination of methane occurs and in a second zone in which the formation of carbon occurs. Within a single reactor, the first zone is in the overhead part since it is the zone where the volatile compounds come into play while the second zone is in the beneath part as carbon is recovered as a solid. Alternatively, step (b) of bromination and synthesis of carbon can be performed within two reactors arranged in series, a first reactor in which the bromination of methane occurs and a second reactor, downstream of said first reactor, in which the formation of carbon occurs.

Step (b) of bromination and synthesis of carbon allows conversion of at least 95 mol % of bromine based on the total bromine introduced into the reactor, preferably of at least 99 mol %.

The reaction of methane with bromine for forming methyl bromides, dibromomethane and tribromomethane as well as the conversion of these products into carbon during step (b) of bromination and synthesis of carbon can be summarized as followed:

$$CH_4 + nBr_2 \rightarrow CH_{4-n}Br_n + nHBr \quad \text{(i)}$$

$$CH_3Br + Br_2 \rightarrow C + 3HBr \quad \text{(ii)}$$

$$CH_2Br_2 \rightarrow C + 2HBr \quad \text{(iii)}$$

$$CHBr_3 \rightarrow C + HBr + Br_2 \quad \text{(iv)}$$

Reaction (i) generally occurs with a fairly high selectivity to methyl bromide, namely $CH_3Br$. For instance, in the case of the non-catalyzed bromination of methane operated with excess methane in the range of about 2.5:1 to about 12:1, preferably of about 3:1 to about 10:1, more preferably of about 4:1 to about 9:1, the reaction selectivity may be above 50% for methyl bromide and less than 40% dibromomethane, on a molar basis.

It is believed that only very small amounts of tri-brominated methane and tetra-brominated methane should also be formed in the bromination reaction. Higher alkanes, such as ethane, propane, and butane, may also be readily also readily brominated resulting in mono- and multi-brominated alkanes, such as brominated ethane, brominated propane, and brominated butane.

To promote the formation of dibromomethane, and by this way to promote the formation of carbon through reaction (iii), the person skilled in the art may take advantage of working at high temperatures such as a temperature of at least 500° C., and preferably at least 550° C.

As it will be seen later, the formation of dibromomethane is also favoured by recycling methyl bromides exiting the bromination and synthesis unit 13 back to the bromination and synthesis unit 13. In the case where the reactor comprises two zones, the methyl bromides are recycled back to the first zone in which the bromination reaction occurs. Similarly, in the case where two reactors are arranged in series, the methyl bromides are recycled back to the first reactor.

In the present disclosure, the formed carbon is easily removed as a solid-state compound.

As can be seen from these four chemical reactions involved in the present disclosure, there is no formation of carbon dioxide.

Step (b) of bromination and synthesis of carbon can be performed in the absence of a catalyst or in the presence of a catalyst. With preference, it is performed in the absence of a catalyst.

However, in case the presence of a catalyst is desirable, examples of suitable catalysts that may be utilized during step (b) of bromination and synthesis of carbon, include, but are not limited to, platinum, palladium, or supported non-stoichiometric metal oxy-halides such as $FeO_xBr_y$ or $FeO_x Cl_y$, or supported stoichiometric metal oxy-halides such as $TaOF_3$, $NbOF_3$, $ZrOF_2$, $SbOF_3$ as described in Olah, et al, *J. Am. Chem. Soc.*, 1985, 107, 7097-7105.

Step (b) of bromination and synthesis of carbon results in the formation of a third stream 15 comprising methyl bromides and hydrogen bromide, and of a fourth stream 25 comprising carbon. The third stream 15 may further comprise bromine, in an amount of 5 mol % or less of the total molar content of said third stream 15, preferably in an amount of 1 mol % or less.

The third stream 15 comprising methyl bromides and hydrogen bromide is then conveyed to a separation unit 19 arranged downstream the bromination and synthesis unit 13. The separation unit 19 comprises one or more distillation column and/or one or more adsorption column and/or one or more absorption column.

For example, the separation unit 19 comprises a first column 21 being a distillation column, or an adsorption column, or an absorption column, configured to separate methyl bromides from the other component of the third stream 15. With preference, said first separation step is performed at a temperature lower than the temperature used in step (b) of bromination and synthesis, for example at a temperature of at least 50° C. lower than the temperature used in the operating conditions of step (b) of bromination and synthesis of carbon. The installation 1 may comprise a heat exchanger 17 arranged between the bromination and synthesis unit 13 and the separation unit 19.

A methyl bromides-rich stream 23 is recovered and preferably recycled to the or one of the reactors of the bromination and synthesis unit 13. This ensures the additional generation of dibromomethane to enhance the yield of carbon. It is preferred that the methyl bromides-rich stream 23 comprises only methyl bromide ($CH_3Br$).

Figure 1:
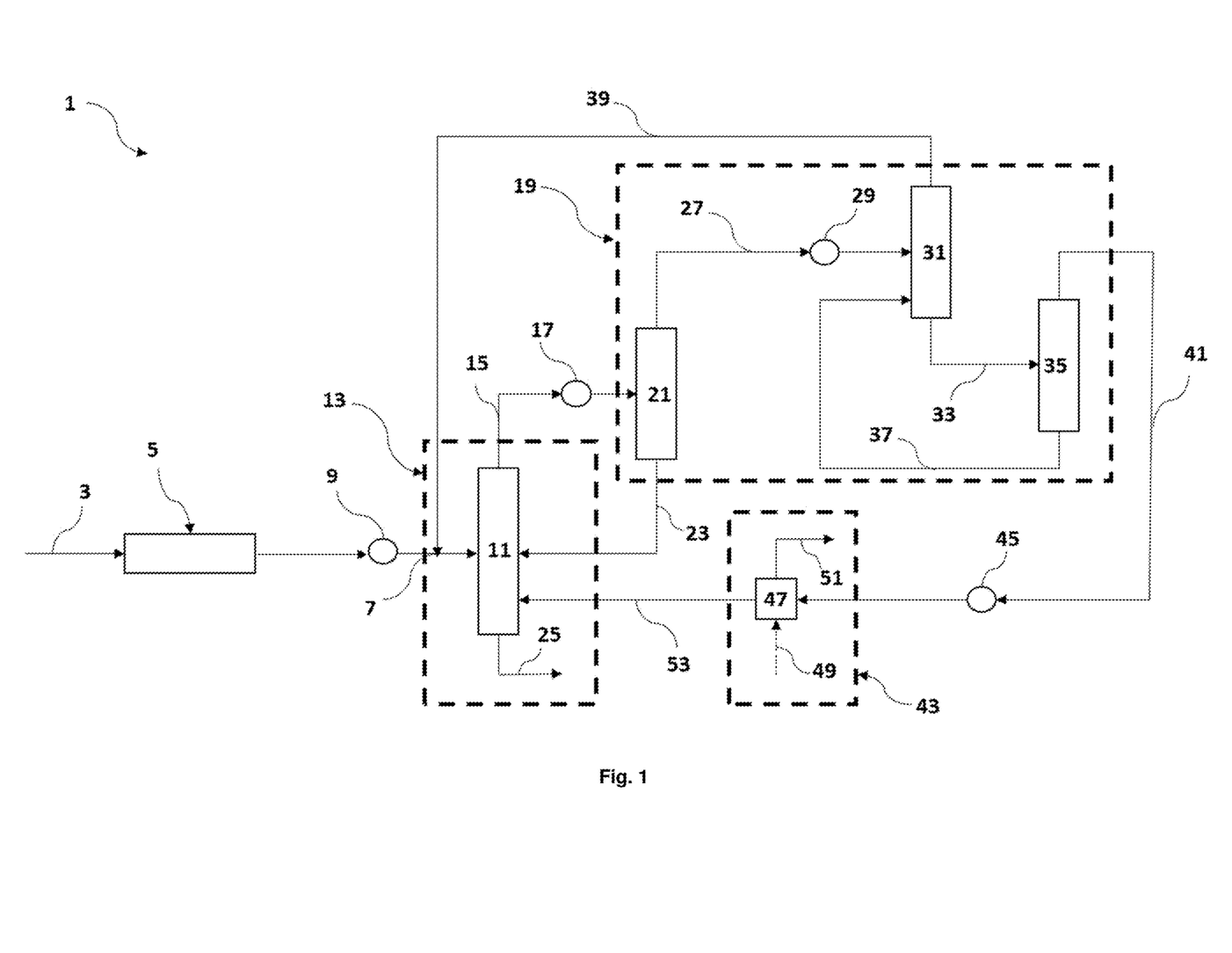
FIG. 1 illustrates the installation per the present disclosure, wherein step (c) of the process is carried out in a non-aqueous phase and in which the step (d) of converting the hydrogen bromide-rich stream into a stream comprising hydrogen and a stream comprising bromine is performed by electrolysis under gaseous phase.
Figure 2:
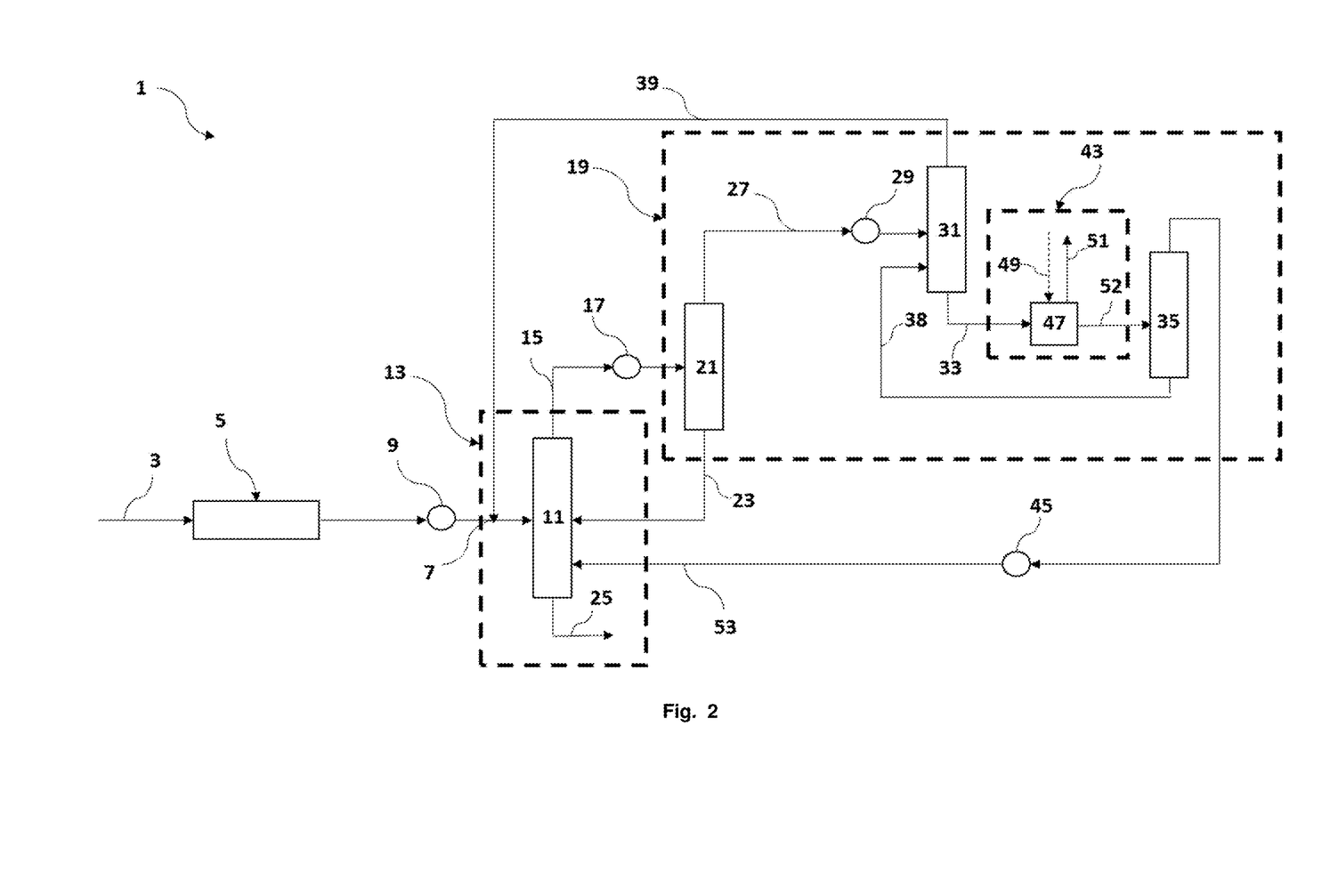
FIG. 2 illustrates the installation per the present disclosure, wherein step (c) of the process is carried out in a non-aqueous phase and in which the step (d) of converting the hydrogen bromide-rich stream into a stream comprising hydrogen and a stream comprising bromine is performed by electrolysis under liquid phase.

The hydrogen bromide-rich stream 27 exiting the first column 21 may comprise unreacted methane and therefore can be submitted to one or more further separation steps such as a step of separation of unreacted methane from the remaining components. This step can be performed in an extractive distillation system, comprising one or more separation columns (31, 35) as shown in FIGS. 1, 2 and 4 or in a decantation system, comprising a water stripper column 97 and a decanter 103, as shown on FIG. 3. For example, the hydrogen bromide-rich stream 27 is passed through one extractive distillation column 31, which is loaded with at least one solvent, such as alcohol, carboxylic acid, ketone, organobromine compounds, ionic liquid, organic acid anhydride and/or nitrile. For example, the solvent is acetic acid. The hydrogen bromide which is contained in the hydrogen bromide-rich stream 27 is thus absorbed on said specific solvent, which allows the separation of the unreacted methane and then the production of a stream 39 comprising unreacted methane. With preference, said stream 39 is recycled into the first gaseous stream (3,7) comprising methane and/or into the one or more of the reactors 11 of the bromination and synthesis unit 13.

Stream 39 comprising unreacted methane may be purged (not shown), which produces fuel gas that can be recovered.

First Embodiment

In the installation, as shown in FIG. 1, once the separation of the unreacted methane has occurred, the remaining stream 33 exiting the extractive distillation column 31 is directed to a second separation column 35 of the extractive distillation system to recover the solvent which was used in the extractive distillation column 31, and to produce a hydrogen bromide stream 41. Said second separation column 35 is preferably a distillation column. The recovered solvent 37 is preferably redirected to the extractive distillation column 31 so that the generation of the hydrogen bromide stream 41 can be continuously achieved.

Installation 1 may comprise one or more heat exchangers 29 arranged between the first column 21 and the extractive distillation system so that one or more steps of adjusting the temperature of the stream 27 before it enters the extractive distillation system is included.

The hydrogen bromide stream 41 is then conveyed to an electrolysis unit 43, optionally after one or more steps of adjusting its temperature in one or more heat exchangers 45, to produce a stream 51 comprising hydrogen and a stream 53 comprising bromine. More particularly, the hydrogen bromide stream 41 can be directed in an electrolysis cell 47, being preferentially a gas-phase electrolysis cell. The gas-phase electrolysis cell can be a proton exchange membrane reactor and is supply with an energy stream 49, consisting preferentially of non-fossil renewable energy (i.e. green electricity).

Second Embodiment

In a second installation illustrated in FIG. 2, once the separation of unreacted methane has occurred, the remaining stream 33, comprising hydrogen bromide and the specific solvent that was used in the extractive distillation column 31, is directed to one electrolysis unit 43 to produce a steam 51 comprising hydrogen and a stream 52 comprising bromine, unconverted hydrogen bromide and said specific solvent.

More particularly, the remaining stream 33 is directed in an electrolysis cell 47, being preferentially a liquid-phase electrolysis cell. The liquid-phase electrolysis cell is supplied with an energy stream 49, comprising preferentially non-fossil renewable energy (i.e. green electricity coming from solar energy and/or wind energy).

Installation 1 may comprise one or more heat exchangers 29 arranged between the first column 21 and the extractive distillation system so that one or more steps of adjusting the temperature of the stream 27 before it enters the extractive distillation system is included.

The stream 52 exiting the electrolysis unit 43 is then conveyed into a separation column 35 to recover the solvent which was used in the extractive distillation column 31, and to produce a bromine-rich stream 41. With the unconverted hydrogen bromide being absorbed on said specific solvent, it is possible to separate the bromine and form a stream 53 comprising bromine. The recovered stream 38 which comprises a mixture of said specific solvent and hydrogen bromide is preferably redirected to the extractive distillation column 31 so that the generation of the stream 53 comprising bromine can be continuously achieved.

Also, to remove any traces of hydrogen bromide in the stream 53 comprising bromine, it is possible to convey the stream 53 comprising bromine into a decanter (not shown) to remove further traces of hydrogen bromide from the stream 53 comprising bromine before being redirected into the bromination and synthesis unit 13, optionally after one or more steps of adjusting its temperature in one or more heat exchangers 45.

Third Embodiment

Figure 3:
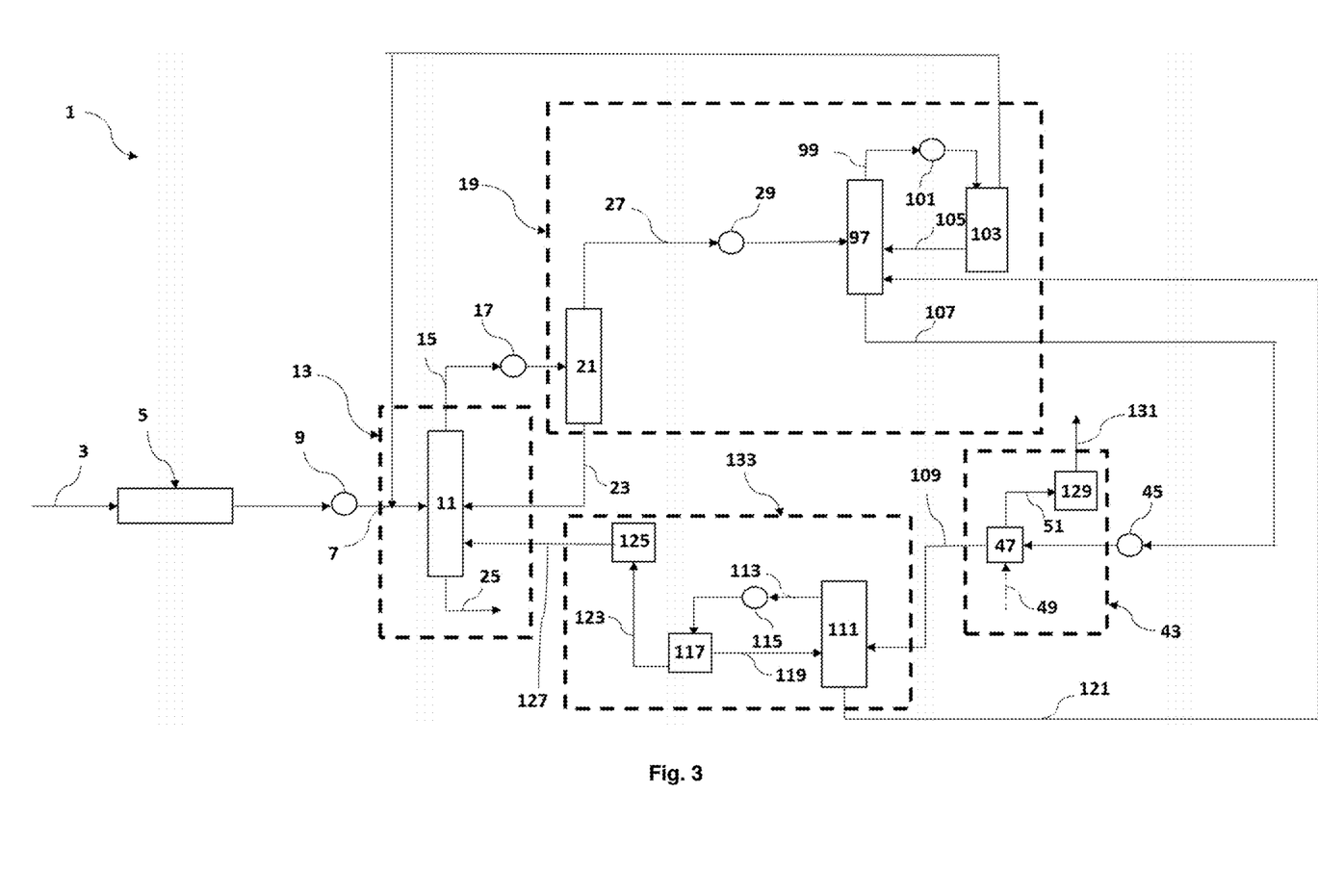
FIG. 3 illustrates the installation per the present disclosure, wherein step (c) of the process is carried out in an aqueous phase and in which the step (d) of converting the hydrogen bromide-rich stream into a stream comprising hydrogen and a stream comprising bromine is performed by electrolysis carried out under aqueous phase.
Figure 4:
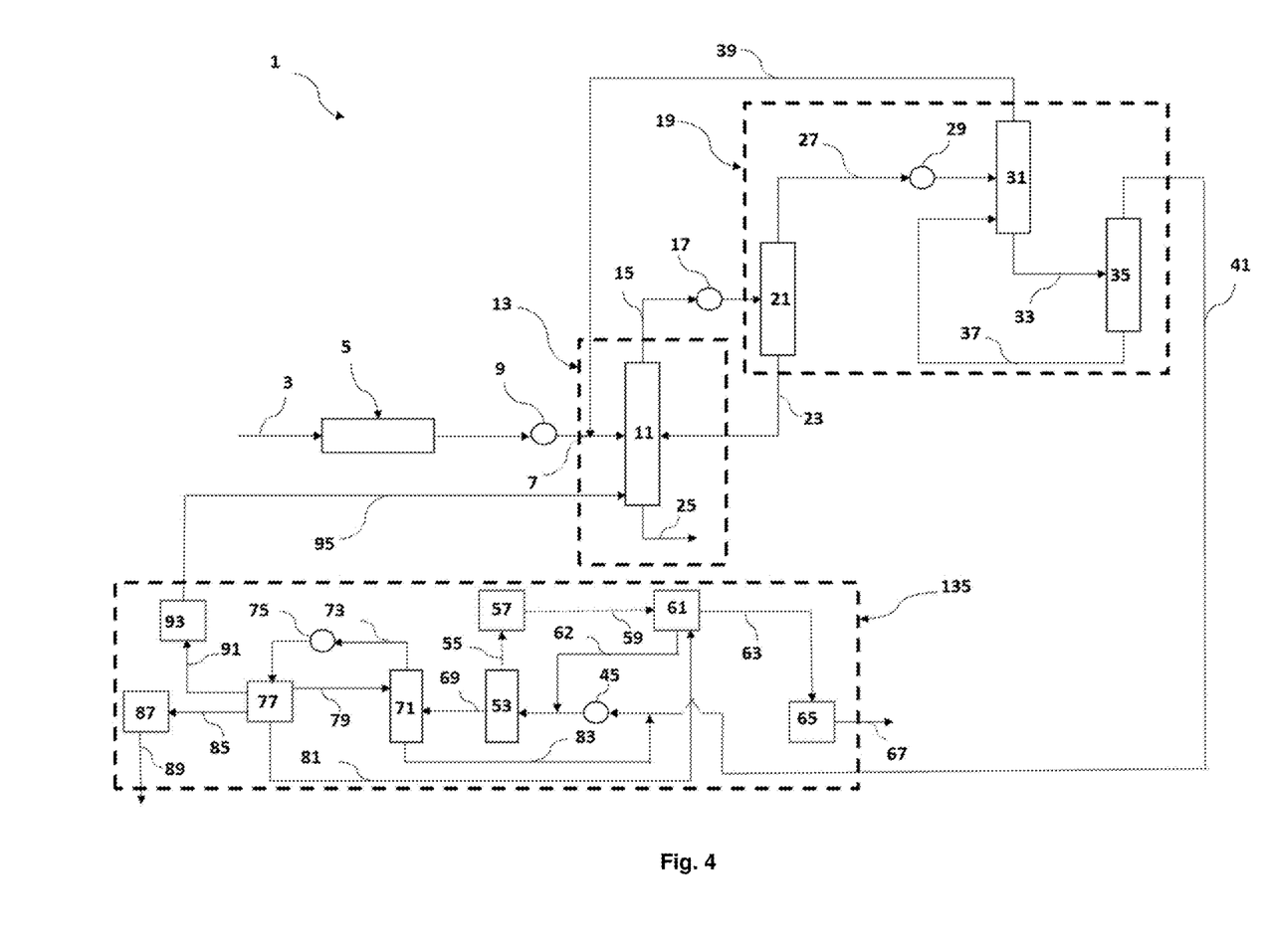
FIG. 4 illustrates the installation per the present disclosure, wherein step (c) of the process is carried out in a non-aqueous phase and in which the step (d) of converting the hydrogen bromide-rich stream into a stream comprising hydrogen and a stream comprising bromine is performed in presence of an oxygen stream.

In a third installation illustrated on FIG. 3, the hydrogen bromide-rich stream 27 exiting the first column 21 is passed through a water stripper column 97, in which the hydrogen bromide is stripped/exchanged against water. For example, the water stripper column 97 is a column with a packed bed composed of Raschig ring. This leads to the formation of a hydrogen bromide stream 107 also comprising water that is expulsed from the separation unit 19. The water stripper column 97 thus allows the separation of a methane stream 99, which, optionally after a step of adjusting its temperature in one or more heat exchangers 101, enters into a decanter 103 to remove the water. A water stream 105 exiting the decanter 103 is reintroduced into the water stripper column 97 to further removed hydrogen bromide from the hydrogen bromide-rich stream 27. Upon decantation of water, a stream 39 comprising methane is obtained.

Said stream 39 comprising methane can be recycled into the first stream (3, 7) comprising natural gas and/or into the one or more of the reactors 11 of the bromination and synthesis unit 13.

The installation 1 may comprise one or more heat exchangers 29 arranged between the first column 21 and the water stripper column 97 so that one or more steps of adjusting the temperature of the stream 27 before it enters the water stripper column 97 is included.

Then, the hydrogen bromide stream 107 comprising water, exiting the separation unit 19, is then conveyed to an electrolysis unit 43 to produce a stream 51 comprising hydrogen and a stream 109 comprising aqueous bromine and unconverted hydrogen bromide. The hydrogen stream 51, before being recovered, can be optionally dried in a drier system 129 to recover a dried gaseous hydrogen stream 131. For example, the drier system 129 is a desiccant. For example, the desiccant can be a molecular sieve, such as one or more zeolite from the LTA family. Among the LTA family, zeolites from LTA-3A, LTA-4A and/or LTA-5A can be selected. In another example, the drier system 129 is a hydrogen drying system as described in US2016/0129390. For example, the drier system 129 works under room temperature, such as between 15° C. and 25° C., and/or under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

The stream 109 comprising aqueous bromine and unconverted bromide also comprises hydrogen bromide that is generated due to the hydrolysis of bromine into the water. The stream 109 comprising aqueous bromine can then be conveyed into a bromine-recovery unit 133, comprising a washing tower 111. The washing tower 111 allows the separation of a hydrogen bromide stream 121 that can be optionally recycled into the water stripper column 97 of the separation unit 19. Also exiting from the washing tower 111, a stream 113 comprising aqueous bromine and possibly traces of hydrogen bromide is directed to an optional decantation system 117 of the bromine-recovery unit 133, possibly via one or more heat exchangers 115. In this decantation system 117, the hydrogen bromide is further separated into a hydrogen bromide stream 119 and optionally recycled into the washing tower 111. The stream 123 comprising bromine exiting the optional decantation system 117 can be dried in a dryer system 125 to produce a stream 127 comprising bromine, that can be optionally reused in the bromination and synthesis unit 13. For example, the dryer system 125 is a desiccant. For example, the desiccant can be a molecular sieve, such as one or more zeolite from the LTA family. Among the LTA family, zeolites from LTA-3A, LTA-4A and/or LTA-5A can be selected.

Fourth Embodiment

In a fourth installation illustrated in FIG. 4, once the separation of the unreacted methane has occurred, the remaining stream 33 exiting the extractive distillation column 31 is directed to a second separation column 35 of the extractive distillation system to recover the solvent which was used in the extractive distillation column 31 and to produce a hydrogen bromide-rich stream 41. Said second separation column 35 is preferably a distillation column. The extractive distillation system as described provides the advantage that the hydrogen bromide-rich stream 41 does not comprise water. The recovered solvent 37 is preferably redirected to the extractive distillation column 31 so that the generation of the hydrogen bromide-rich stream 41 can be continuously achieved.

With preference, the hydrogen bromide-rich stream 41 comprises only hydrogen bromide. Thus, the hydrogen bromide-rich stream 41, exiting the separation unit 19, is conveyed to a conversion unit 135 to produce a stream (63, 67) comprising hydrogen and a stream (69, 91, 95) which is a bromine-rich stream. More particularly, the hydrogen bromide-rich stream 41 can be directed in a conversion reactor 53, optionally after one or more steps of adjusting its temperature in one or more heat exchangers 45. For example, the conversion reactor 53 can be a multi-tubular fixed bed reactor or a shell and tube heat exchanger reactor, preferably a shell and tube heat exchanger reactor. The conversion of the hydrogen bromide-rich stream 41 is carried out in the presence or in the absence of one or more catalysts. For example, in the conversion reactor 53, hydrogen bromide is let to react with oxygen ($O_2$) in gas phase. The conversion reaction operates preferably at the tube side of the shell and tube heat exchanger reactor. For example, the pressure conditions of the conversion reactor are comprised between 0.5 MPa and 1.5 MPa, preferably between 0.7 MPa and 1.2 MPa. For example, the temperature conditions of the conversion reaction are comprised between 500° C. and 600° C., preferably between 520° C. and 580° C.

When the conversion of the hydrogen bromide-rich stream 41 is carried out in the presence of one or more catalysts, it is advantageous to use a shell and tube heat exchanger reactor, so that the one or more catalyst can be installed in the tube side. For example, the one or more catalysts are metal-oxides supported on alumina. Further details about the one or more catalysts can be found in US 2011/0015458, the content of which is incorporated by reference.

The conversion of hydrogen bromide into bromine is an exothermic reaction (i.e. the heat reaction is about −69 kJ/mol of hydrogen bromide). The shell and tube heat exchanger reactor allow recovering the heat by vaporizing at the shell side of the shell and tube heat exchanger reactor water into a high-pressure stream. Thus, the shell side of the shell and tube heat exchanger can act as a steam generator which can be included in a thermodynamic steam cycle for power production. Preferably, the steam cycle is composed of a feed water pump for compression, preferably an isentropic compression; a steam generator for heat addition, preferably for isobaric heat addition; a steam turbine for expansion, preferably for isentropic expansion; and a condenser for heat rejection, preferably for isobaric heat rejection. It is expected that about 30% to 50% thermodynamic efficiency leads to 0.006 (69/3600*30%) to 0.01 (69/3600*50%) kWh of produced work per mole of HBr oxidized. The thermodynamic efficiency has been determined by simulation via ASPEN PLUS V9 software.

To maximize the energy management of the installation, the thermal energy 55 recovered from the conversion reactor 53 that has been transferred to water can be further converted into electrical energy 59 thanks to its passage within a steam-electric power sub-unit 57. For example, the steam-electric power sub-unit 57 can be a steam turbine.

The electrical energy 59 serves then to feed a water electrolysis reactor 61, for example, an alkaline electrolysis cell, a proton-exchange membrane electrolysis cell or a solid oxide electrolysis cell. This configuration is interesting in the sense that it prevents the use of external electricity supply for the water electrolysis reactor 61.

Said electrolysis reaction of water is advantageously carried out under pressure conditions ranging between 0.1 MPa and 20 MPa, preferably between 0.5 MPa and 17 MPa, more preferably between 1 MPa and 15 MPa. Said electrolysis reaction of water can also be carried out under temperature conditions ranging between 50° C. and 1000° C., preferably between 75° C. and 975° C., more preferably between 100° C. and 900° C. Said electrolysis reaction of water is advantageously carried out upon consumption between 3 kWh/$m^3$ of hydrogen produced and 6 kWh/$m^3$ of hydrogen produced, preferably between 3.5 kWh/$m^3$ of hydrogen produced and 5.5 kWh/$m^3$ of hydrogen produced.

Knowing the potential difference for water electrolysis of −1.23 V, the system requires a theoretical minimal energy supply of 237 kJ/mol. This means that to recover one ton of oxygen, the electrolysis cell theoretically needs 2060 kWh for 100% hydrogen bromide conversion and assuming 100% energy efficiency. Water is electrically split into a hydrogen stream (63, 67) and an oxygen stream 62.

The hydrogen stream 63 can be further dried over a drier system 65. For example, the drier system 65 is a desiccant. For example, the desiccant can be a molecular sieve, such as one or more zeolite from the LTA family. Among the LTA family, zeolites from LTA-3A, LTA-4A and/or LTA-5A can be selected. In another example, the drier system 65 is a hydrogen drying system as described in US2016/0129390. For example, the drier system 65 works under room temperature, such as between 15° C. and 25° C., and/or under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

The oxygen stream 62 is advantageously mixed with the hydrogen bromide-rich stream 41 before entering the conversion reactor 53, as shown in FIG. 4. The oxygen stream 62 can also be directed directly into the conversion reactor 53 (not shown). The oxygen stream 62 is thus the oxidant used in the conversion of hydrogen bromide. By using such oxidant, the thermal energy 55 recovered from the conversion reactor 53 during the conversion step is at least partially recycled, which therefore improved the energy management of the described installation. Alternatively, the thermal energy 55, or the corresponding electrical energy 59, could be re-directed in another installation. In that case, a cheap and easy-to-handle oxidant for working the conversion reaction could be the use of air.

The bromine-rich stream 69 exiting the conversion reactor 53 comprises traces of water and subsequently forms hydrogen bromide by hydrolysis. The bromine-rich stream 69 comprising thus a mixture of bromine and hydrogen bromide is advantageously directed into a washing tower 71, which allows separating a first part of hydrogen bromide from said mixture. Following this separation, the aqueous hydrogen bromine stream 83 exiting the washing tower 71 can be optionally redirected upstream of the conversion reactor 53, for additional recovery by conversion of hydrogen bromide into bromine. The stream 73 exiting the washing tower comprises the remaining part of said mixture and can be directed, optionally after one or more steps of adjusting its temperature in one or more heat exchangers 75, to a decantation sub-unit 77.

The optional decantation sub-unit 77 allows the separation on one hand of the bromine, to recover a bromine-rich stream 91, and on the other hand of the hydrogen bromide in gaseous form and in aqueous form (respectively, a gaseous stream (85, 89) and an aqueous stream 79). Finally, water can be recovered, forming a water stream 81, and can be advantageously conveyed into the water electrolysis reactor 61.

The bromine-rich stream 91 exiting the optional decantation sub-unit 77 is preferably dried in a dryer system 93 to produce the bromine-rich stream 95 that exits the conversion unit 135 and that can be optionally redirected in the bromination and synthesis unit 13. For example, the dryer system 93 is a desiccant. For example, the desiccant can be a molecular sieve, such as one or more zeolite from the LTA family. Among the LTA family, zeolites from LTA-3A, LTA-4A and/or LTA-5A can be selected.

The gaseous stream 85 can be optionally passed through a purification column 87 to eliminate any residual traces of bromine. The removal of the gaseous stream 85 allows the optional decantation sub-unit 77 to diminish the internal pressure and to make it work efficiently.

The aqueous stream 79 can be optionally redirected into the washing tower 71, so that the aqueous hydrogen bromide is either redirected on a line upstream to the conversion reactor 53 or redirected into the optional decantation sub-unit 77.

The following two half-reactions occurring in the electrolysis unit 43 present in the installation shown in FIGS. 1, 2 and 3 can be summarized as follows:

$$2Br^- \rightarrow Br_2 + 2e^-$$

$$2H^+ + 2e^- \rightarrow H_2$$

The electrolysis is advantageously carried out in a gas phase and can be for example achieved in a proton-exchange membrane electrolysis cell. When such kind of electrochemical cells is used, it may comprise an anode side and a cathode side, the anode side and the cathode side is separated by a proton-conducting membrane, for example, a proton-conducting membrane made in ceramic materials. For example, when the step (d) of electrolysis is carried out in the gas phase, the step (d) of electrolysis is performed under temperature conditions ranging between 300° C. and 700° C., preferably between 325° C. and 675° C., more preferably between 375° C. and 625° C. For example, when the step (d) of electrolysis is carried out in the liquid phase, including the aqueous phase, the step (d) of electrolysis is performed under temperature conditions ranging between 20° C. and 80° C., preferably between 25° C. and 70° C., more preferably between 30° C. and 40° C. For example, whichever the phase in which the step (d) of electrolysis is carried out, the step (d) of electrolysis is performed under pressure conditions of at least 0.1 MPa, preferably ranging between 0.1 MPa and 2.0 MPa, more preferably ranging between 0.5 MPa and 1.5 MPa, even more preferably ranging from 0.6 MPa to 1.0 MPa.

Knowing the potential difference for hydrogen bromide electrolysis of −1.07 V, the system requires a theoretical minimal energy supply of 206 kJ/mol. This means that to recover one ton of bromine, the electrolysis cell theoretically needs 358 kWh for 100% hydrogen bromide conversion and assuming 100% energy efficiency.

The regenerated stream comprising bromine exiting from the electrolysis unit can be preferentially used in the bromination unit, either by being mixed with the methane stream before entering the bromination unit or by being directly conveyed into the bromination reactor. When the process comprises this recycling step, there is no net consumption of bromine, because it is fully regenerated in the process.

The electrolysis of hydrogen bromine stream allows the formation of hydrogen as a pure stream product and avoids the use of oxidative bromine recovery routes. This is advantageous in the sense it prevents the consumption of oxygen coming from air separation units that are a cumbersome technique. Also, the use of bromine recovery by electrolysis allows preventing the generation of water contaminated with bromine as end-products, which occurs when oxidative bromine recovery routes are used. Therefore, the subsequent treatment of water is not necessary.

Recovery of the Fourth Stream 25 Comprising Carbon

An optional purification of the carbon can be carried out. Analysis of the carbon by scanning electron microscope (SEM) coupled with energy dispersive X-ray spectroscopy (EDS) can be also performed.

Figure 5:
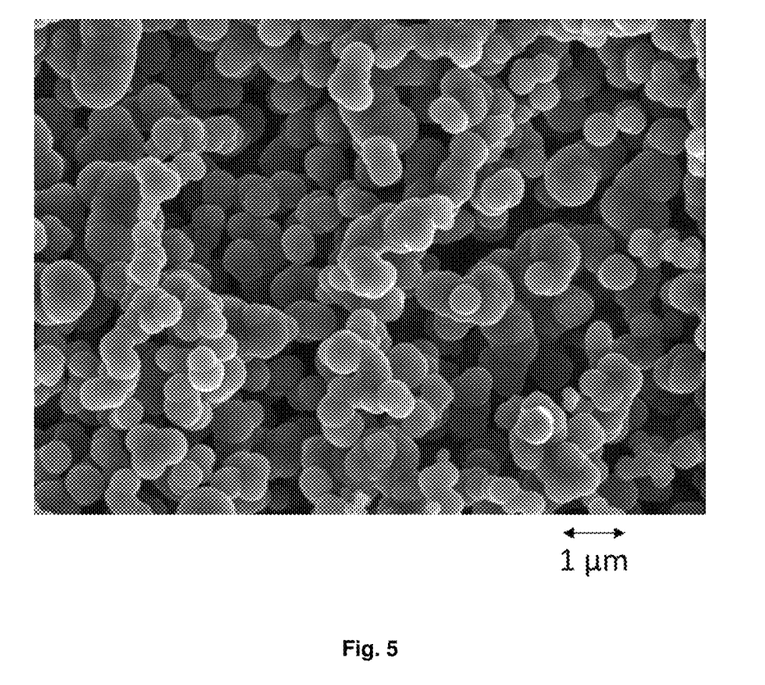
FIG. 5 is a scanning electron microscope-energy dispersive X-ray spectroscopy (SEM-EDS) image of the carbon after purification.

FIG. 5 shows an SEM-EDS image of the carbon that has been purified over a purification procedure. Such purification procedure comprises placing the carbon sample in a boat crucible at 600° C. for at least 3.5 hours under a 5% $H_2/N_2$ flow (200 ml/min) in a tube furnace. The average content after purification: carbon purity can reach >99.9 wt. %, and bromide was reduced to 0.05 wt. % (0.01 atomic %).

Test and Determination Methods

Raman Spectroscopy

The Raman spectra were collected on a Horiba Jobin Yvon, LabRAM HR using 785 and 532 nm lasers and ×50 long-distance lens. The density filter was additionally applied to reduce the laser power <1 mW and avoid sample decomposition. Spectra were obtained by accumulating 10 scans with an integration time of 5 s. Spectrometer was calibrated using Si polycrystalline plate as a standard with a characteristic band at 520.6 cm$^{-1}$.

Energy-Dispersive X-Ray Spectroscopy (EDX)

The energy dispersive X-ray spectra were gathered using SUPRA 35 VP (Carl Zeiss) field emission scanning electron microscope equipped with required detectors.

Example

Figure 6:
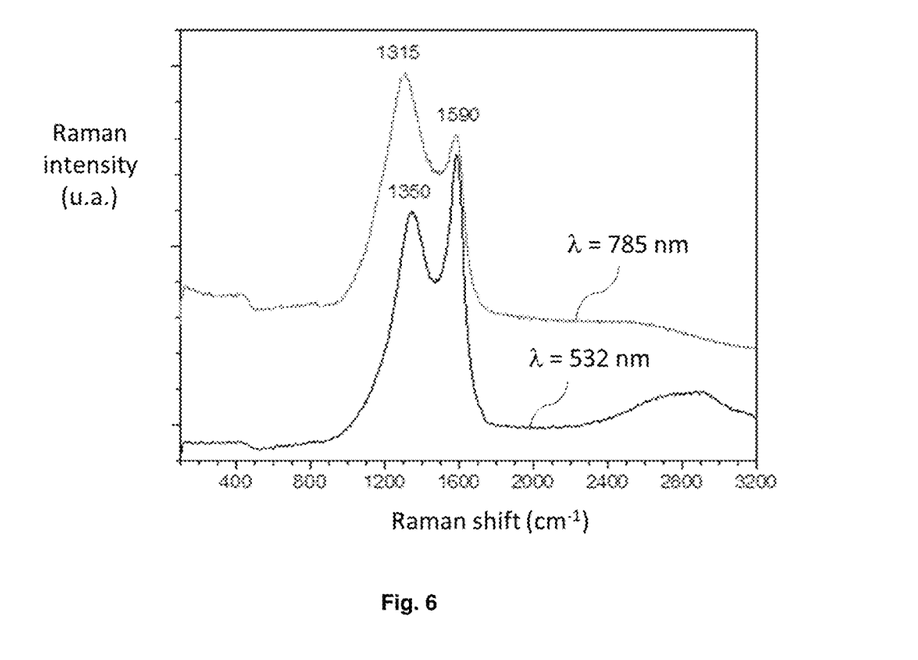
FIG. 6 is a Raman spectrum of carbon black samples isolated from the reactor.

In an example, a pre-heated feed stream comprising 40 wt. % of $Br_2$, 10 wt. % of $CH_2Br_2$, 10 wt. % of $CH_3Br$ and balance of methane was used in a carbonization step performed in an INCONEL tubular reactor equipped with a trap for solids down to the heated zone. The temperature during reaction was ranging between 600 and 800° C. along the reactor. The gaseous effluent gas was bubbled through a solution containing 30 wt. % of NaOH to neutralize forming HBr. Total amount of $CH_2Br_2$ and $CH_3Br$ fed into the reactor was about 200 g. After the test, the reactor was flushed with pure argon and black solid from the trap was discharged. FIG. 6 is a Raman spectrum of the solid and corresponds to carbon black in the form of agglomerates with ~1 μm linear dimension. 1 g of said solid was placed in a quartz boat and carbonized in a flow of $N_2$ with rate 200 ml/min at 800° C. (ramp rate 10° C./min). The treated solid has been collected and analyzed by means of EDX spectroscopy. Mass content of Br element appeared to be inferior to 0.04 wt. % as based on the total content of the 1 g of solid product.

The invention claimed is:

1. A process of conversion of gaseous stream comprising methane into hydrogen (51, 63) and carbon (25), said process is characterized in that it comprises the following steps:
   a step (a) of providing a first gaseous stream (3, 7) comprising methane;
   a step (b) of bromination and synthesis of carbon wherein the first gaseous stream (3, 7) comprising methane of step (a) is put in contact with a second stream (53, 95, 127) comprising bromine under operating conditions resulting in the formation of a third stream (15) comprising methyl bromides and hydrogen bromide, and of a fourth stream (25) comprising carbon including graphite and/or carbon black;
   a step (c) of separation performed on the third stream (15) to recover a hydrogen bromide-rich stream (33, 41, 107) and a methyl bromides-rich stream (23), wherein the process comprises a step of recycling the methyl bromides-rich stream (23) into step (b) of bromination and synthesis of carbon; and
   a step (d) of converting said hydrogen bromide-rich stream (33, 41, 107) into a stream (51, 63) comprising hydrogen and a stream (53, 95, 127) comprising bromine.

2. The process according to claim 1, characterized in that said step (c) is performed by non-aqueous extraction and in that said step (d) of converting said hydrogen bromide-rich stream (33, 41) is performed by electrolysis of said hydrogen bromide-rich stream (33, 41).

3. The process according to claim 1, characterized in that said step (c) is performed by aqueous extraction and in that said step (d) of converting said hydrogen bromide-rich stream (107) is performed by electrolysis carried out in aqueous phase to produce a stream comprising bromine (109, 127).

4. The process according to claim 1, characterized in that said step (c) is performed by non-aqueous extraction and in that said step (d) of converting said hydrogen bromide-rich stream (41) is carried out in presence of an oxygen stream (62), to produce a bromine-rich stream (69, 91, 95).

5. The process according to claim 4, wherein said step (d) of converting said hydrogen bromide-rich stream (33, 41, 107) into a stream (51, 63) comprising hydrogen and a stream (53, 95, 127) comprising bromine further produces thermal energy (55), further wherein said thermal energy (55) is converted into electrical energy (79).

6. The process according to claim 5, characterized in that said electrical energy (79) is used in an electrolysis reaction of water to produce a hydrogen stream (63, 67) and/or an oxygen stream (62) which is optionally used in said step (d) of converting said hydrogen bromide-rich stream (33, 41, 107) into a stream (51, 63) comprising hydrogen and a stream (53, 95, 127) comprising bromine.

7. The process according to claim 1, characterized in that step (c) of separation comprises at least one step of separation of hydrogen bromide to produce a hydrogen bromide-rich stream (27), wherein said hydrogen bromide-rich stream (27) is subjected to one or more further steps of separation.

8. The process according to claim 1, characterized in that the operating conditions of step (b) include one or more of a temperature ranging from 500° C. to 1000° C., a pressure ranging from 0.1 MPa to 2.0 MPa, and being performed without catalyst.

9. The process according to claim 1, characterized in that step (c) of separation is performed at a temperature lower than the temperature used in step (b) of bromination and synthesis of carbon.

10. The process according to claim 1, characterized in that step (c) of separation comprises at least one step of separation of a stream (39) comprising unreacted methane.

11. The process according to claim 1, characterized in that the process comprises a step of recycling the stream (53, 95, 127) comprising bromine obtained in step (d) into step (b) of bromination and synthesis of carbon.

12. The process according to claim 1, characterized in that step (a) of providing a first gaseous stream (3) comprising methane comprises providing a natural gas comprising methane at a content of at least 75 mol. % of the total molar content of said natural gas.

13. The process according to claim 1, characterized in that step (a) of providing a first gaseous stream (3) comprising methane comprises providing natural gas and purifying the natural gas to remove one or more selected from sulphur, nitrogen, water, oxygen and carbon dioxide.

14. The process according to claim 1, characterized in that in step (b) comprises a carbonization step performed on the fourth stream at a temperature ranging from 500° C. to 3500° C.

* * * * *

UNITED STATES PATENT AND TRADEMARK OFFICE
CERTIFICATE OF CORRECTION

PATENT NO. : 11,891,706 B2
APPLICATION NO. : 17/915958
DATED : February 6, 2024
INVENTOR(S) : Romuald Coupan, Nikolai Nesterenko and Gleb Veryasov It is certified that error appears in the above-identified patent and that said Letters Patent is hereby corrected as shown below:

On the Title Page

Item (71), please delete the second Applicant city "Winterhur" and replace with "Winterthur".

Signed and Sealed this
Twenty-sixth Day of March, 2024

Katherine Kelly Vidal
*Director of the United States Patent and Trademark Office*